United States Patent [19]

Sturm

[11] 4,017,627
[45] Apr. 12, 1977

[54] 7,8-DISUBSTITUTED-5-ACETYLQUINO-LINES AND ANTIMICROBIAL COMPOSITIONS CONTAINING THEM

[75] Inventor: Elmar Sturm, Aesch, Switzerland

[73] Assignee: Ciba-Geigy Corporation, Ardsley, N.Y.

[22] Filed: May 19, 1975

[21] Appl. No.: 578,584

[30] Foreign Application Priority Data

May 29, 1974 Switzerland ............... 7321/74

[52] U.S. Cl. .................. 424/258; 260/287 L; 260/287 XA
[51] Int. Cl.² ............ C07D 215/32; C07D 215/34; A61K 31/47
[58] Field of Search ............. 260/287 L; 424/258

[56] References Cited

UNITED STATES PATENTS

| | | | |
|---|---|---|---|
| 2,666,058 | 1/1954 | Neher | 260/287 L |
| 2,875,126 | 2/1959 | Hodel et al. | 260/287 L |
| 3,793,314 | 2/1974 | Navdi et al. | 260/287 L |

FOREIGN PATENTS OR APPLICATIONS 974,981  2/1961  United Kingdom ........... 260/287 L Primary Examiner—Donald G. Daus
Assistant Examiner—David E. Wheeler
Attorney, Agent, or Firm—Karl F. Jorda; Edward McC. Roberts; Prabodh I. Almaula

[57] ABSTRACT

7,8-Disubstituted-5-acetylquinolines and antimicrobial compositions containing said compounds are disclosed.

17 Claims, No Drawings

7,8-DISUBSTITUTED-5-ACETYLQUINOLINES AND ANTIMICROBIAL COMPOSITIONS CONTAINING THEM

The present invention relates to 7,8-disubstituted-5-acetylquinolines of the formula I

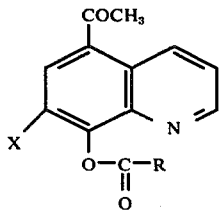

wherein X denotes chlorine, bromine, iodine or nitro, R denotes optionally hologen-substituted $C_1$–$C_{16}$ alkyl or $C_2$–$C_{10}$ alkenyl; $C_1$–$C_4$ alkoxy, $C_2$–$C_4$ alkenyloxy, $C_1$–$C_4$ alkylthio or optionally methyl-substituted $C_3$–$C_6$ cycloalkyl or cycloalkoxy; or $C_3$–$C_6$ cycloalkenyl or phenyl which is optionally substituted by nitro, halogen or $C_1$–$C_3$ alkyl, a process for the manufacture of these compounds and agents and their use for combating micro-organisms.

All alkyl, alkenyl, alkoxy, alkenyloxy, and alkylthio groups can be straight-chain or branched.

Alkyl or the alkyl part of an alkoxy or alkylthio group is to be understood, depending on the number of carbon atoms indicated, as, for example, the following groups: methyl, ethyl, propyl, butyl, pentyl, hexyl, octyl, nonyl, decyl, undecyl, dodecyl, tetradecyl, pentadecyl or hexadecyl and their isomers such as, for example, isopropyl, iso-, sec- or tert.-butyl, 1-methylbutyl, 2-ethylhexyl and the like.

Alkenyl or the alkenyl part of an alkenyloxy group is to be understood, depending on the number of carbon atoms indicated, as, for example, the following groups: vinyl, prop-l-enyl, butenyl, dec-9-en-l-yl or 1,3-pentadienyl and their isomers such as, for example, isopropenyl, 2-methyl-prop-l-enyl or 2-methyl-but-2-enyl.

The following groups, for example, are suitable as $C_3$–$C_6$ cycloalkyl, cycloalkoxy or cycloalkenyl: cyclopropyl (oxy), cyclopentyl(oxy), cyclohexyl(oxy), cyclobutenyl, cyclohexenyl and the like. These groups can optionally be substituted by one or more methyl groups.

The halogens which are optionally present as substituents are fluorine, chlorine, bromine or iodine.

An interesting group of compounds of the formula I is formed by those wherein R denotes $C_1$–$C_4$ alkyl or $C_2$–$C_{10}$ alkenyl which are optionally substituted by hologen; $C_1$–$c_4$ alkoxy, $C_2$–$C_4$ alkenyloxy, $C_1$–$C_4$ alkylthio or cyclohexyl which is optionally substituted by methyl; or cyclohexenyl or phenyl which is optionally substituted by halogen.

Compounds which are Particularly worthy of note are those of the formula I wherein R denotes $C_1$–$C_4$ alkyl, $C_2$–$C_3$ alkenyl or cyclohexyl.

Five compounds which are preferred owing to their microbicidal action are: 5-acetyl-7-chloro-8-vinylcarbonyloxy-quinoline of the formula

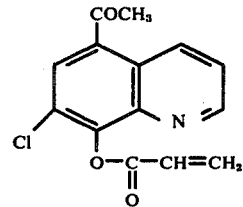

5-acetyl-7-bromo-8-vinylcarbonyl-oxy-quinoline of the formula

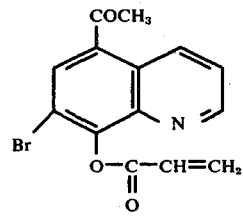

5-acetyl-7-iodo-8-vinylcarbonyloxy-quinoline of the formula

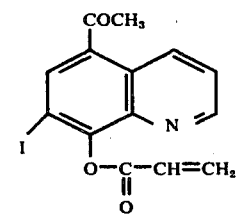

5-acetyl-7-nitro-8-vinylcarbonyloxy-quinoline of the formula

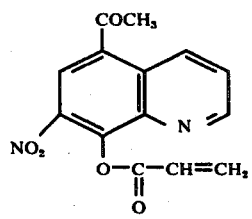

5-acetyl-7-nitro-8-methoxycarbonyloxy-quinoline

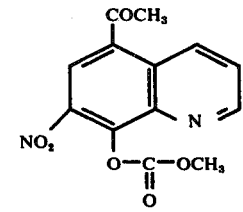

The compounds of the formula I are manufactured in accordance with the invention by reacting a compound of the formula II

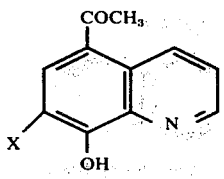

in the presence of a base, with a compound of the formula III

wherein R and X have the meanings indicated under formula I, and Hal represents halogen, preferably chlorine.

Examples of suitable bases are alkali metal hydroxides, carbonates, bicarbonates, acetates or alcoholates or alkaline earth metal hydroxides, carbonates, bicarbonates, acetates or alcoholates as well as tertiary amines and other nitrogencontaining bases, such as, for example, triethylamine or pyridine.

The reactions are carried out, where appropriate, in solvents or diluents which are inert towards the reactants. The following should be mentioned as examples: acetone, tetrahydrofurane, benzene, dioxane, toluene and the like or 2-phase systems, such as, for example, methylene chloride, chloroform, benzene or toluene together with aqueous alkali metal hydroxides or alkali metal carbonates and the like.

The process is carried out at temperatures between 0° and 60° C and at normal pressure.

The starting substances of the formula II wherein X denotes chlorine, bromine or iodine, are manufactured by methods of halogenation which are in themselves known.

5-Acetyl-8-hydroxyquinoline of the formula

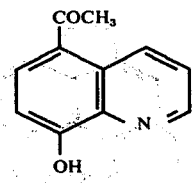

is reacted, for example, with an alkali metal hypohalite, such as sodium hypochlorite, hypobromite or hypoiodite in a polar solvent, such as, for example, glacial acetic acid. It is also possible to employ other halogenating agents, such as, for example, N-halogenosuccinimide or the free halogens. The starting material of the formula II, wherein X denotes nitro, is manufactured in a manner which is in itself known by nitration. 5-Acetyl-8-hydroxyquinoline is reacted, for example, with nitric acid and sodium nitrate in a polar solvent, such as glacial acetic acid.

The compounds of the formula II, wherein X denotes chlorine or nitro, are also a subject of the invention.

The compounds of the formula I are distinguished by a broad microbicidal action. Thus they can be employed against phytopathogenic fungi, such as, for example, fungi which attack the above-ground parts of plants. The following examples of such species of fungi can be mentioned: phycomycetes (oomycetales), for example *Phytophthora infestans* and *Plasmopara viticola*; ascomycetes, for example *Erysiphe cichoracearum*, *Erysiphe graminis*, *Podosphaera leucotricha* and *Venturia inaequalis*; basidiomycetes, for example *Uromyces phaseoli*, *Puccinia graminis tritici* and *Fungi imperfecti*, for example *Botrytis cinerea*, *Piricularia oryzae*, *Septoria apicola* and *Alternaria solani*. Seed-borne fungi and those which attack from the soil can also be combated. Amongst these the following representatives from the abovementioned classes are to be understood, for example: representatives of the order Fusarium, for example *Fusarium nivale* or *Fusarium oxysporum*, Helminthosporium, for example *Helminthosporium gramineum* or *Helminthosporium maydis*, Tilletia, for example *Tilletia caries* or *Tilletia controversa*, Ustilago, for example *Ustilago nuda* or *Ustilago avenae* and Puthium, Verticillium, Aphanomyces and, for example, *Rhizoctonia solani* or *Septoria nodorum*. The compounds can also be employed as seed dressings in order to combat these fungi.

The compound of the formula II wherein X denotes chlorine also has fungicidal properties.

The compounds of the formula I also have an action against phytopathogenic bacteria on cereals, maize, potatoes, rice, vegetables, vines, ornamental plants, fruit and other crops.

Representatives of the order Pseudomonas, for example *Pseudomonas tomato*, *Pseudomonas lachrymans* and *Pseudomonas phaseolicola*, Xanthomonas, for example *Xanthomonas oryzae*, *Xanthomonas vesicatoria* and *Xanthomonas phaseoli*, and Erwinia and Corynebacterium can be mentioned, inter alia, as phytopathogenic bacteria.

In order to adapt them to the circumstances of a given case, the compounds of the formula I can of course also be employed conjointly with other suitable pesticides, such as, for example, fungicides, bactericides, insecticides, acaricides, menaticides or active compounds which influence plant growth, in order to broaden or to modify in other ways their spectrum of action.

The compounds of the formula I can be used on their own or conjointly with suitable carriers and/or other additives. Suitable carriers and additives can be solid or liquid and correspond to the materials which are customary in formulation technology, such as, for example, natural or regenerated mineral materials, solvents, dispersing agents, wetting agents, adhesives, thickeners, binders or fertilisers.

The compounds of the formula I can be present in the following process forms for application:
solid process forms: dusting agents, sprinkling agents, granules, coated granules, impregnated granules and homogeneous granules.
liquid process forms:
 a. concentrates of active substance dispersible in water: wettable powders, pastes, or emulsions;
 b. solutions.

For the manufacture of solid process forms (dusting agents and sprinkling agents) the active compounds are mixed with solid carriers. Examples of suitable carriers which can be used are kaolin, talc, bolus, loess, chalk, limestone, limestone grit, attapulgite, dolomite, diatomaceous earth, precipitated silica, alkaline earth metal silicates, sodium aluminium silicates and potassium aluminium silicates (feldspars and micas), calcium sulphates and magnesium sulphates, magnesium oxide, ground plastics, fertilisers, such as ammonium sulphate, ammonium phosphate, ammonium nitrate or urea, ground vegetable products, such as cereal flour, treebark flour, wood flour, nut shell flour, cellulose powder, residues of plant extracts, active charcoal and the like, in each case on their own or as mixtures with one another.

Granules can be manufactured by dissolving an active compound of the formula I in an organic solvent and applying the solution obtained in this way to a granulated mineral, for example attapulgite, $SiO_2$, granicalcium, bentonite and the like and then again evaporating the organic solvent.

Polymer granules can be prepared by impregnating, for example, a finished, porous granular polymer (urea/formaldehyde, polyacrylonitrile, polyester and others) having a particular surface area and a favourable predetermined absorption/desorption ratio, with the active compounds, for example in the form of their solutions (in a low-boiling solvent and removing the solvent. Such polymer granules can also be applied, in the form of micro-granules with bulk densities of, preferably, 300 g/liter to 600 g /liter, with the aid of dust sprayers. The dust spraying can be carried out over large areas of crop plant cultures, by means of aircraft.

Granules are also obtainable by compacting the carrier material together with the active compounds and additives and then comminuting the product.

It is further possible to add to these mixtures additives which stabilise the active compound and/or non-ionic, anionic and cationic compounds which, for example, improve the adhesion of the active compounds to plants and parts of plants (adhesives and glues) and/or ensure better wettability (wetting agents) and dispersibility (dispersing agents).

For example, the following compounds can be used: olein/lime mixture, cellulose derivatives (methylcellulose and carboxymethylcellulose), hudroxyethylene glycol ethers of monoalkylphenols and dialkylphenols with 5–15 ethylene oxide residues per molecule and 8–9 carbon atoms in the alkyl radical, ligninsulphonic acid, its alkali metal salts and alkaline earth metal salts, polyethylene glycol ethers (Carbowax), fatty alcohol polyglycol ethers with 5–20 ethylene oxide residues per molecule and 8–18 carbon atoms in the fatty alcohol part, condensation products of ethylene oxide and propylene oxide, polyvinylpyrrolidone, polyvinyl alcohols, condensation products or urea/formaldehyde and latex products.

Water-dispersible active compound concentrates, that is to say wettable powders, pastes and emulsion concentrates are agents which can be diluted with water to any desired concentration. They consist of active compound, carrier, where appropriate additives which stabilise the active compound, surface-active substances and anti-foaming agents and, if appropriate, solvents.

The wettable powders and pastes are obtained by mixing and grinding the active compounds with dispersing agents and pulverulent carriers in suitable apparatuses until the mixture is homogeneous. Examples of carriers which can be used are those mentioned above for the solid process forms. In some cases, it is advantageous to use mixtures of different carriers. Examples of dispersing agents which can be used are condensation products of sulphonated naphthalene and sulphonated naphtalene derivatives with formaldehyde, condensation products of naphthalene or naphthalenesulphonic acid with phenol and formaldehyde, and alkali metal salts, ammonium salts and alkaline earth metal salts of ligninsulphonic acid, as well as alkylarylsulphonates, alkali metal salts and alkaline earth metal salts of dibutylnaphthalenesulphonic acid, fatty alcohol-sulphates, such as salts of sulphated hexadecanols, heptadecanols and octadecanols and salts of sulphated fatty alcohol glycol ethers, the sodium salt of oleyl methyl tauride, di-tertiary ethylene glycols, dialkyldilaurylammonium chloride and fatty acid salts of alkali metals and alkaline earth metals.

Examples of anti-foaming agents which can be used are silicone oils.

The active compounds are mixed, ground, sieved and graded together with the abovementioned additives so that in the wettable powders the solid constituent has a particle size of 0.02 to 0.04 mm and in the pastes the particle size does not exceed 0.03 mm. To prepare emulsion concentrates and pastes, dispersing agents, as have been listed in the preceding paragraphs, organic solvents and water are used. Examples of possible solvents are alcohols, benzene, xylenes, toluene, dimethylsulphoxide and mineral oil fractions boiling in the range from 120 to 350°C. The solvents must be practically odourless, non-phytotoxic and inert towards the active compounds.

Furthermore, the agents according to the invention can be used in the form of solutions. For this purpose, the active compound or several active compounds of the general formula I are dissolved in suitable organic solvents, solvent mixtures or water. As organic solvents it is possible to use aliphatic and aromatic hydrocarbons, their chlorinated derivatives, alkylnaphthalenes and mineral oils, individually or as mixtures with one another.

The content of active compound in the agents described above is between 0.1 and 95%.

The active compounds of the formula I can, for example, be formulated as follows:

Dusting agents

The following compounds are used to prepare a) a 5% strength dusting agent and b) a 2% strength dusting agent:

a. 5 parts of active compound and 95 parts of talc;
b. 2 parts of active compound, 1 part of highly disperse silica and 97 parts of talc.

The active compounds are mixed, and ground, with the carriers.

Granules

The following compounds are used to prepare 5% strength granules:

5 parts of active compound, 0.25 part of epichlorohydrin, 0.25 part of cetyl polyglycol ether, 3.50 parts of polyethylene glycol and 91 parts of kaolin (particle size 0.3-0.8 mm.).

The active compound is mixed with the epichlorohydrin and dissolved is 6 parts of acetone, after which the polyethylene glycol and cetyl polyglycol ether are added. The solution thus obtained is sprayed onto kaolin and the acetone is then evaporated in vacuo.

Wettable powder

To prepare a) a 40% strength wettable powder, (b) and (c) a 25% wettable powder and (d) a 10% strength wettable powder, the following constituents are used:

a. 40 parts of active compound, 5 parts of the sodium salt of ligninsulphonic acid, 1 part of the sodium salt of dibutylnaphtalenesulphonic acid and 54 parts of silica.

b. 25 parts of active compound, 4.5 parts of calcium ligninsulphonate, 1.9 parts of Champagne chalk/hydroxyethylcellulose mixture (1:1), 1.5 parts of sodium dibutylnaphthalenesulphonate, 19.5 parts of silica, 19.5 parts of Champagne chalk and 28.1 parts of kaolin;

c. 25 parts of active compound, 2.5 parts of isooctylphenoxypolyoxyethylene-ethanol, 1.7 parts of Champagne chalk/hydroxyethylcellulose mixture (1:1), 8.3 parts of sodium aluminium silicate, 16.5 parts of kieselguhr and 46 parts of kaolin;

d. 10 parts of active compound, 3 parts of a mixture of the sodium salts of saturated fatty alcohol-sulphates, 5 parts of naphthalenesulphonic acid/formaldehyde condensate and 82 parts of kaolin.

The active compounds are intimately mixed with the additives in suitable mixers and ground on appropriate mills and rolls. Wettable powders which can be diluted with water to give suspensions of any desired concentration are obtained.

Emulsifiable concentrates

To prepare a 25% strength emulsifiable concentrate, the following compounds are used:

a. 25 parts of active compound, 2.5 parts of epoxidised vegetable oil, 10 parts of an alkylarylsulphonate/fatty alcohol polyglycol mixture, 5 parts of dimethylformamide and 57.5 parts of xylene.

Emulsions of any desired concentration can be prepared from such concentrates by dilution with water.

Furthermore, the active compounds of the formula I can be used against ubiquitous fungi and bacteria for the purpose of preserving organic materials such as timber, paper, plastics, paints and the like, and as disinfectants, for example in soaps, washing agents and rinses. By ubiquitous fungi and bacteria there are to be understood, for example, the following micro-organisms: *Candida albicans, Aspergillus niger, Staphylococcus aureus, Escherichia coli* or *Salmonella sp.*

The following may be mentioned as examples of products which can be preserved with the aid of the compounds according to the invention: glues,, binders, paints, textile auxiliaries and textile finishing agents, pigment pastes and printing pastes and similar preparations based on organic dyestuffs or pigments, including those which include casein or other organic compounds as admixtures. Paint coats on walls and ceilings, for example paint coats which contain a pigment binder which contains albumin, are also protected against attack by pests through adding the compounds according to the invention. The compounds can also be used to protect timber.

The compounds according to the invention can also be employed as preservatives in the cellulose and paper industry.

The action of the compounds according to the invention can also be utilised in preservative and disinfectant finishes for plastics. When using plasticisers it is advantageous to add the antimicrobial additive to the plastic as a solution or dispersion in the plasticiser. It is desirable to ensure that the additive is as uniformly distributed in the plastic as possible. The plastics with antimicrobial properties can be used for consumer goods of all kinds in which activity against a great diversity of germs, such as, for example, bacteria and fungi, is desired, for example for doormats, bathroom curtains, toilet seats, floor grids in swimming baths, wall coverings and the like. If they are incorporated into suitable wax compositions and polishing compositions, floor polishes and furniture polishes having a disinfectant action are obtained.

Because of their better solubility in organic solvents, the active compounds are also very suitable for application from non-aqueous media. In this case, the materials to be finished and/or protected can simply by impregnated with the solutions. Examples of possible organic solvents are trichloroethylene, methylene chloride, hydrocarbons, propylene glycol, methoxyethanol, ethoxyethanol and dimethylformamide, to which agents to assist distribution (for example emulsifiers such as sulphonated castor oil, fatty alcohol-sulphates and the like) and/or other auxiliaries can also be added.

By combination of the compounds according to the invention with surface-active substances, especially detergent substances, washing and cleaning agents having an exellent antibacterial and/or antimycotic action are obtained. Aqueous preparations of such washing and cleaning agents, which contain compounds according to the invention, can be used an antimicrobial cleaning agents in the foodstuff and beverage industry, for example breweries, dairies and abattoirs.

The washing and cleaning agents can be in any desired form, for example in a liquid, pasty, solid, flocculent or granular form. The compounds according to the invention can be incorporated into anionic compounds, such as soaps and other carboxylates (for examaple alkali metal salts of higher fatty acids), derivatives of acids containing sulphur and oxygen (for example the sodium salt of dodecylbenzenesulphonic acid, water-soluble salts of sulphuric acid monoesters of higher-molecular alcohols or their polyglycol ethers, such as, say, soluble salts of dodecyl acohol-sulphate or of dodecyl alcohol polyglycol ether-sulphate), derivatives of acids containing phosphorus and oxygen (for example phosphates), derivatives of acid (electrophilic) nitrogen in the hydrophilic group (for example disulphinic salts), and also cationic surface-active agents, such as amines and their salts (for example lauryldiethylenetriamine), onium compounds and amine oxides, or non-ionic surface-active agents, such as polyhydroxy compounds, surface-active agents based on monosaccharides and polysaccharides, higher molecular acetylene glycols and polyglycol ethers (for example polyglycol ethers of higher fatty alcohols and polyglycol ethers of higher-molecular aralkylated phenols), as well as mixtures of different types of surface-active agents. In these compositions, their antimicrobial activity remains fully preserved. The active compound content of the washing and cleaning agents, relative to the weight of the agent, is in general 0.01 to 5%, and in most cases 0.1 to 5%, and in most cases 0.1 to 3%.

For purposes of disinfection and preservation, the compounds can also be used in combination with known antimicrobial agents.

The examples which follow serve to explain the invention in more detail without limiting it.

EXAMPLE I a. Preparation of 5-acetyl-7-chloro-8-hydroxyquinoline

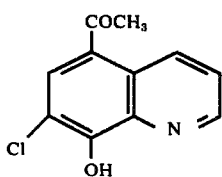

(Compound No. 1)

350 ml of a 14% strength sodium hypochlorite solution are added dropwise to a suspension of 94 g of 5-acetyl-8-hydroxyquinoline in 1 litre of methanol and 1 litre of water at 10°–20°C, whilst stirring well. After stirring for a further hour, the mixture is acidified with 60 ml of glacial acetic acid and diluted with 1 liter of water, and the product is filtered off. The filter residue is washed with water and recrystallised, whilst still moist, from alcohol. 70 g of almost colourless 5-acetyl-7-chloro-8-hydroxyquinoline are obtained, melting point 163°–166° C.

b. Preparation of

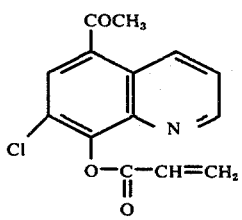

(Compound No. 2)

5-acetyl-7-chloro-8-vinylcarbonyloxyquinoline.

A solution of 22 g of the 5-acetyl-7-chloro-8-hydroxyquiniline in 150 ml of methylene chloride is covered with a solution of 14 of potassium carbonate in 100 ml of water. 9.1 g of freshly distilled acrylic acid chloride are added dropwise to the mixture, whilst stirring well and cooling with ice. After stirring for 1 hour at 20° C, the phases are separated and the methylene chloride solution is evaporated in vacuo. The brown crystalline residue is recrystallised from a benzene/hexane mixture, whereupon 18 g of the compound 2, melting point 120-122° C, are obtained.

EXAMPLE 2

Preparation of

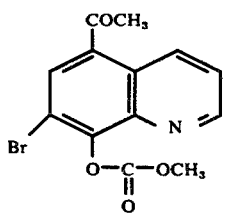

(Compound No. 3)

5-acetyl-7-bromo-8-methoxycarbonyloxyquinoline.

26.6 g of 5-acetyl-7-bromo-8-hydroxyquinoline are dissolved in 200 ml of tetrahydrofurane, 11 g of triethylamine are added and 9.5 g of chloroformic acid methyl ester, diluted in 50 ml of tetrahydrofurane, are added dropwise, whilst stirring and cooling. When the exothermic reaction has ended, the triethylamine hydrochloride which has separated out is removed by filtration and the clear filtrate is evaporated.

The crude crystalline residue is recrystallised from a hexane/benzene mixture, whereupon 21 g of the compound 3, melting point 142°–144° C, are obtained.

EXAMPLE 3

The following compounds of the formula I are prepared analogously to Examples 1 and 2:

| Compound | X | R | Physical data |
|---|---|---|---|
| 4 | Br | —OC$_2$H$_5$ | M.p. 107–109° C |
| 5 | Br | —CH=CH$_2$ | M.p. 129–130° C |
| 6 | Br | —C(CH$_3$)=CH$_2$ | M.p. 124–126° C |
| 7 | Br | —CH=C(CH$_3$)$_2$ | M.p. 119–123° C |
| 8 | Br | —CH$_3$ | M.p. 142–143° C |
| 9 | Br | —C(Br)=CH$_2$ | M.p. 132–134° C |
| 10 | Br | —CH=CH—CH$_3$ | M.p. 144–147° C |
| 11 | Br | cyclohexyl-H | M.p. 107–109° C |
| 12 | Br | —CH=CH—CH=CH—CH$_3$ | M.p. 94–96° C |
| 13 | Br | cyclohexyl-H | viscous oil |
| 14 | Br | methylcyclohexenyl (CH$_3$) | M.p. 91–93° C |
| 15 | Br | 4-chlorophenyl | M.p. 135–137° C |
| 16 | Br | —C(CH$_3$)$_3$ | M.p. 90–94° C |
| 17 | Br | —S—C$_4$H$_9$ | M.p. 79–80° C |
| 18 | Br | 4-nitrophenyl | |
| 19 | I | —CH=CH$_2$ | M.p. 118–120° C |
| 20 | I | —OCH$_3$ | M.p. 106–108° C |
| 21 | I | —CH$_3$ | M.p. 135–138° C |
| 22 | I | —CH=CH—CH$_3$ | M.P. 127–128° C |
| 23 | I | —C(CH$_3$)=CH$_2$ | M.p. 112–114° C |
| 24 | I | cyclohexyl-H | M.p. 106–108° C |
| 25 | I | —CH=C(CH$_3$)$_2$ | M.p. 136–139° C |
| 26 | I | —CH=CH—CH=CH—CH$_3$ | M.p. 133–136° C |
| 27 | I | methylcyclohexyl-H (CH$_3$) | viscous oil |

-continued

| Compound | X | R | Physical data |
|---|---|---|---|
| 28 | I |  | M.p. 192–194° C |
| 29 | I | —CH₂Cl | M.p. 120–123° C |
| 30 | Cl | —C₂H₅ | M.p. 86–88° C |
| 31 | Cl | —OCH₃ | M.p. 138–140° C |
| 32 | Cl | 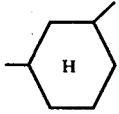 | viscous oil |
| 33 | Cl | —(CH₂)₂CH=CH₂ | viscous oil |
| 34 | Cl | —O—CH₂—CH=CH₂ | M.p. 87–89° C |
| 35 | Cl | 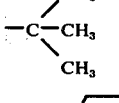 | M.p. 82–86° C |
| 36 | Cl | 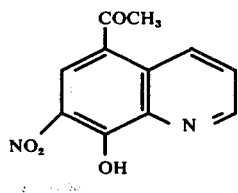 | |
| 37 | Cl | 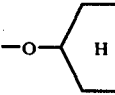 | |
| 38 | Cl | —S—C₂H₅ | |

EXAMPLE 4 a. Preparation of

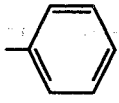

(Compound No. 39)

5-acetyl-7-nitro-8-hydroxyquinoline.

140 ml of approximately 65% strength nitric acid are added dropwise, whilst stirring, to a solution of 374 g of 5-acetyl-8-hydroxyquinoline in 4,000 ml of glacial acetic acid. A thick white precipitate forms. A concentrated aqueous solution of 5 g of sodium nitrite is added to the suspension. A further 140 ml of nitric acid are added dropwise at 35°–40° C. The nitration commences and the temperature remains at 40°–45° C without external supply of heat. The reaction mixture is stirred for a further 2 hours at room temperature and is then poured onto water. The product which has precipitated is filtered off, washed until neutral and dried in vacuo, whereupon 295 g of the compound 39, melting point 280°–290° C (decomposition) are obtained.

Preparation of

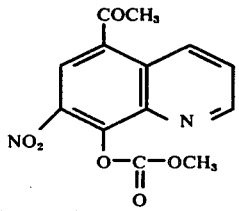

(Compound No. 40)

5-acetyl-7-nitro-8-methoxycarbonyloxyquinoline.

10.5 g of triethylamine are added to a solution of 23 g of 5-acetyl-7-nitro-8-hydroxyquinoline in 150 ml of tetrahydrofurane and 9.5 g of chloroformic acid methyl ester are slowly added dropwise to this mixture.

After completion of the reaction, the triethylamine hydrochloride which has separated out is removed by filtration and the clear filtrate is evaporated in vacuo.

The crystalline residue is recrystallised from hexane/benzene and yields 23 g of compound No. 40, which melts at 126°–128° C.

EXAMPLE 5

The following compounds of the formula I are prepared analogously to Example 4.

| Compound No. | X | R | Physical data |
|---|---|---|---|
| 41 | NO₂ | —CH=CH₂ | M.p. 112–114° C |
| 42 | NO₂ | —OCH₂—CH=CH₂ | M.p. 76–78° C |
| 43 | NO₂ | —C≡CH₂<br>    \|<br>   CH₃ | M.p. 114–116° C |
| 44 | NO₂ | 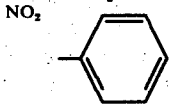 | M.p. 127–130° C |
| 45 | NO₂ | —CH₃ | |
| 46 | NO₂ | —CH₂Cl | |
| 47 | NO₂ | —(CH₂)ₙ—CH=CH₂ | |
| 48 | NO₂ | 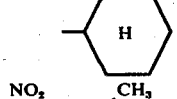 | |
| 49 | NO₂ | 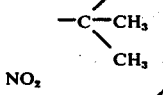 | |
| 50 | NO₂ | 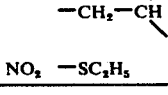 | |
| 51 | NO₂ | —SC₂H₅ | |

EXAMPLE 6 a. Action against *Botrytis cinerea* on *Vicia faba*

Vicia plants about 10 cm high were sprayed with a spray liquor (0.05% active compound) prepared from wettable powders of the active compound. After 48 hours, the treated plants were infected with a suspension of conidia of the fungus. After incubating the infected plants for 3 days at 95–100% relative atmospheric humidity and 21° C, the fungal attack was assessed.

b. Action against *Erysiphe cichoracearum* on *Cucurbita pepo*

Courgette plants in the cotyledon stage were sprayed with a spray liquor (0.05% active compound) prepared from wettable powders of the active compound. After 48 hours, the treated plants were dusted with conidia of the fungus. The infected plants were set up in a greenhouse at about 22° C and the fungal attack was assessed after 10 days.

c. Action against *Podosphaera leucotricha* on Malus sylvestris

Apple cuttings with about 15 cm long new shoots were sprayed with a spray liquor (0.05% active substance) prepared from wettable powders of the active compound. After 24 hours, the treated plants were infected with a suspension of conidia of the fungus and set up in a climatic chamber at 70% relative atmospheric humidity and 20° C. The fungal attack was assessed 12 days after the infection.

d. Action against *Venturia inaequalis* on *Malus sylvestris*

Apple cuttings with 10–20 cm long new shoots were sprayed with a spray liquor (0.05% active substance) prepared from wettable powders of the active compound. After 24 hours the treated plants were infected with a suspension of conidia of the fungus. The plants were then incubated for 5 days at 90–100% relative atmospheric humidity and set up for a further 10 days in a greenhouse at 20°–24° C. The attack by scab was assessed 15 days after infection.

e. Action against *Helminthosporium gramineum*

Helminthosporium gramineum is cultured in Erlenmeyer flasks on autoclaved oat grains and used to infect wheat, which is then dressed with 500 ppm of active substance (as a wettable powder) by shaking in a flask. The grains treated in this way are laid out on a malt/peptone/agar nutrient medium in Petri dishes (25 grains/dish) and set up at 20° to 24° C for 3 days. Evaluation takes place through counting the grains which have been attacked.

e. Action against *Piricularia oryzae* on *Oryzae sativa*

Rice plants were grown for two weeks and then sprayed with a spray liquor (0.05% active substance) prepared from wettable powders of the active compound. After 48 hours, the treated plants were infected with a suspension of conidia of the fungus. After incubation for 5 days at 95–100% relative atmospheric humidity and 24° C, the fungal attack was assessed.

f. Action against *Puccinia graminis* F. sp. *secalis* on *Secale cereale*

Rye plants were sprayed, 4 days after sowing, with a spray liquor (0.05% active substance) prepared from wettable powders of the active compound. After 24 hours, the treated plants were infected with a uredospore suspension of the fungus. After an incubation of 48 hours at 95–100% relative atmospheric humidity and about 20° C, the infected plants were set up in a greenhouse at about 22° C.

The development of the rust pustules was assessed 12 days after infection.

The following compounds showed a good action in the case of the following fungi (that is to say, less than 20% attack on the plants, compared with untreated but infected control plants): in the case of *Botrytis cinerea*, compounds No. 40, 5, 2, 20, 18 and 1; in the case of *Erysiphe cichoracearum*, compounds No. 5, 2, 20 and 18; in the case of *Podospharera leucotricha*, compounds No. 2 and 5; in the case of *Venturia inaequalis*, compound No. 40; in the case of *Helminthosporium gramineum*, compounds No. 1 and 2; in the case of *Piricularia oryzae*, compounds No. 40 and 2; in the case of *Puccinia graminis*, compounds No. 40, 5, 2 and 1.

EXAMPLE 7 a. Action against *Pseudomonas lachrymans* on cucumbers (*Cucumis sativus*)

Cucumbers were grown for 12 days in a greenhouse and then sprayed with the test substance in the form of a spray liquor (concentration 0.1% of active substance) until dripping wet. After the sprayed coating had dried on, the plants were set up in a climatic chamber at 24° C and about 95% relative atmospheric humidity. 24 hours later, the plants were infected by spraying the underside of the primary leaves with a standardised suspension of *Pseudomonas lachrymans*. After 8 days' incubation in the same chamber, large angular blotches permeated by water formed on these leaves. The number of such blotches per primary leaf served as a basis of assessing the activity of the test substance. Compounds 18, 20, 2, 5, 40 and 12 showed a good action at 1,000 ppm (that is to say less than 20% attack on the plants, compared with the untreated but infected control group).

b. Action against *Xanthomonas vesicatoria* paprika (*Capsicum annuum*)

Paprika plants were grown for 3 weeks in a greenhouse and then sprayed with the test substance in the form of a spray liquor (concentration 0.1% of active substance) until dripping wet. After the sprayed coating had dried on, the plants were set up in a climatic chamber at 24° C and about 95% relative atmospheric humidity. 24 hours later, the plants were infected by spraying the underside of the primary leaves with a standardised suspension of *Xanthomonas vesicatoria*. After 8 days' incubation in the same chamber, dark green, subsequently brown, blotches formed on the leaves. The average number of blotches per leaf served as a basis of assessing the activity of the test substance. Compounds 18, 12, 20, 2, 5 and 40 showed a good action at 1,000 ppm (that is to say less than 20% attack on the plants, compared with the untreated but infected control group).

c. Action against *Pseudomonas phaseolicola* on beans (*Phaseolus vulgaris*).

Bean plants were grown for 8 days in a greenhouse and then sprayed with the test substance in the form of a spray liquor (concentration 0.1% of active substance) until dripping wet. After sprayed coating had dried on, the plants were set up in a climatic chamber at 24° C and about 95% relative atmospheric humidity. 24 hours later, the plants were infected by spraying the underside of the primary leaves with a standardised suspension of Pseudomonas phaseolicola. After 8 days' incubation in the same chamber, dot-shaped water-permeated blotches with a yellow halo formed on these leaves. The average number of such blotches per leaf served as a basis of assessing the activity of the test substance. Compounds 12 and 40 showed a good action at 1,000 ppm (that is to say less than 20% attack on the plants, compared with the untreated but infected control group).

EXAMPLE 8

Action against ubiquitous bacteria and fungi

The active compounds are absorbed on various types of fabric (cotton, nylon and polyester) from ethoxyethanol/dimethylformamide solutions, in such a way that the active compounds are present in concentrations of 1%, 0.5% and 0.25% on the fabric. Agar (nutrient agar and Mycosel agar) is poured into Petri dishes and inoculated, after setting, with the following test organisms:

Bacteria: Staphylococcus aureus, Escherichia coli, Proteus mirabilis and Pseudomonas aeruginosa.

Fungi: Candida albicans, Trichophyton mentagrophytes and Aspergillus niger.

Discs (diameter 20 mm) of the treated fabric are placed on the inoculated agar plates. The dishes are then incubated for 24 hours at 37° C (bacteria and Candida) or 3 to 4 days at 28° C (fungi). The action is then assessed by measuring the zone of inhibition around the test disc or by observation of growth under the discs.

In this test, the following compounds showed an excellent microbicidal action: compounds No. 2, 5, 40, 20, 21, 12 and 18.

What I claim is:

1. A 7,8-disubstituted-5-acetylquinoline of the formula

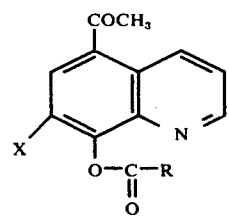

wherein X denotes chlorine, bromine, iodine or nitro, R denotes unsubstituted or halogen-substituted $C_1$–$C_{16}$ alkyl or $C_2$–$C_{10}$ alkenyl; $C_1$–$C_4$ alkoxy, $C_2$–$C_4$ alkenyloxy, $C_1$–$C_4$ alkylthio, unsubstituted or methyl-substituted $C_3$–$C_6$ cyclohexyl; cyclohexenyl or unsubstituted or nitro, halogen or $C_1$–$C_3$ alkyl substituted phenyl.

2. A 7,8-disubstituted-5-acetylquinoline according to claim 1, wherein R denotes unsubstituted or halogen-substituted $C_1$–$C_4$ alkyl or $C_2$–$C_{10}$ alkenyl; $C_1$–$C_4$ alkoxy, $C_2$–$C_4$ alkenyloxy, $C_1$–$C_4$ alkylthio, unsubstituted or methyl-substituted cyclohexyl, cyclohexenyl or unsubstituted or halogen-substituted phenyl.

3. A 7,8-disubstituted-5-acetylquinoline according to claim 1, wherein R denotes $C_1$–$C_4$ alkyl, $C_2$–$C_3$ alkenyl or cyclohexyl.

4. A 7,8-disubstituted-5-acetylquinoline according to claim 1 of the formula

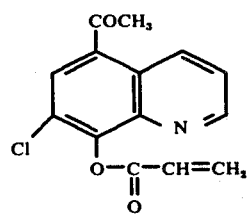

5. A 7,8-disubstituted-5-acetylquinoline according to claim 1 of the formula

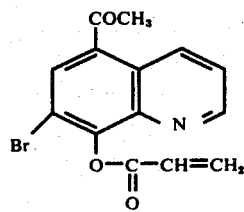

6. A 7,8-disubstituted-5-acetylquinoline according to claim 1 of the formula

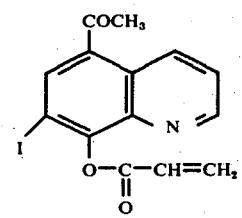

7. A 7,8-disubstituted-5-acetylquinoline according to claim 1 of the formula

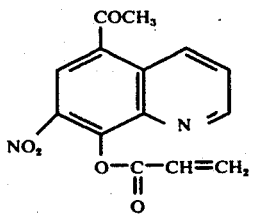

8. A 7,8-disubstituted-5acetylquinoline according to claim 1 of the formula

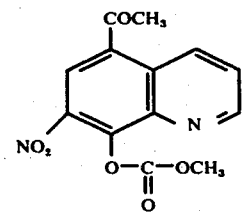

9. A process for combatting phytopathogenic fungi and bacteria which comprises applying to said fungi and bacteria, an inhibitory amount of a compound of the formula

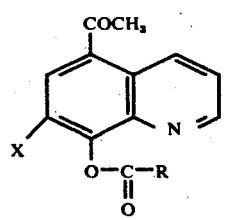

wherein X denotes chlorine, bromine, iodine or nitro, R denotes unsubstituted or halogen-substituted $C_1$–$C_{16}$ alkyl or $C_2$–$C_{10}$ alkenyl; $C_1$–$C_4$ alkoxy, $C_2$–$C_4$ alkenyloxy, $C_1$–$C_4$ alkylthio, unsubstituted or methyl-substituted $C_3$–$C_6$ cyclohexyl; cyclohexenyl or unsubstituted or nitro, halogen or $C_1$-$C_3$ alkyl substituted phenyl.

10. A process according to claim 9 wherein the compound of the formula I

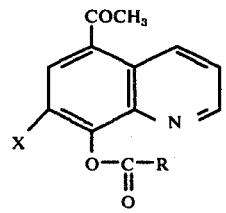

R denotes unsubstituted or halogen-substituted $C_1$-$C_4$ alkyl or $C_2$-$C_{10}$ alkenyl; $C_1$-$C_4$ alkoxy, $C_2$-$C_4$ alkenyloxy, $C_1$-$C_4$ alkylthio, unsubstituted or methyl-substituted cyclohexyl, cyclohexenyl or unsubstituted or halogen-substituted phenyl.

11. A process according to claim 9, wherein in the compound of the formula I

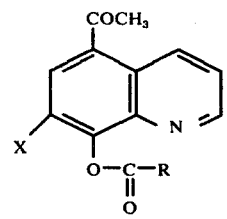

R denotes $C_1$-$C_4$ alkyl, $C_2$-$C_3$ alkenyl or cyclohexyl.

12. An antimicrobial composition for combatting phytopathogenic fungi and bacteria which comprises an inert carrier and an inhibitory amount of a compound of the formula

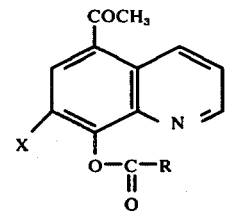

wherein X denotes chlorine, bromine, iodine or nitro, R denotes unsubstituted or halogen-substituted $C_1$-$C_{16}$ alkyl or $C_2$-$C_{10}$ alkenyl; $C_1$-$C_4$ alkoxy, $C_2$-$C_4$ alkenyloxy, $C_1$-$C_4$ alkylthio, unsubstituted or methyl-substituted $C_3$-$C_6$ cyclohexyl cyclohexenyl or unsubstituted or nitro, halogen or $C_1$-$C_3$ alkyl substituted phenyl.

13. A composition according to claim 12 wherein said compound is of the formula

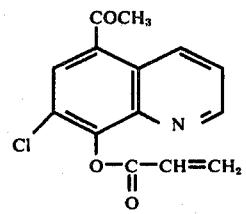

14. A composition according to claim 12 wherein said compound is of the formula

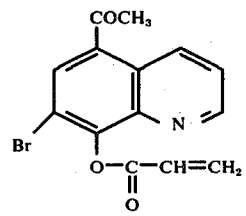

15. A composition according to claim 12 wherein said compound is of the formula

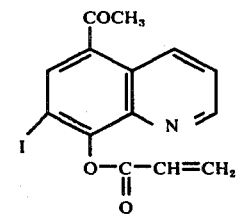

16. A composition according to claim 12 wherein said compound is of the formula

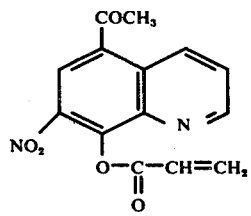

17. A composition according to claim 12 wherein said compound is of the formula

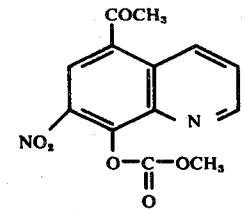

* * * * *

UNITED STATES PATENT OFFICE
CERTIFICATE OF CORRECTION

Patent No. 4,017,627          Dated April 12, 1977

Inventor(s) Elmar Sturm

It is certified that error appears in the above-identified patent and that said Letters Patent are hereby corrected as shown below:

Column 16, claim 9, line 67, delete "$C_3$-$C_6$"

Column 17, claim 12, line 56, delete "$C_3$-$C_6$" same line, insert after "cyclohexyl" -- ; --.

Signed and Sealed this twelfth Day of July 1977

[SEAL]

Attest:

RUTH C. MASON
Attesting Officer

C. MARSHALL DANN
Commissioner of Patents and Trademarks